United States Patent
Ege et al.

(10) Patent No.: US 9,708,426 B2
(45) Date of Patent: Jul. 18, 2017

(54) LIQUID-SOLID SAMPLING SYSTEM FOR A LOOP SLURRY REACTOR

(71) Applicant: Chevron Phillips Chemical Company LP, The Woodlands, TX (US)

(72) Inventors: Stephen L. Ege, Houston, TX (US); Ralph W. Romig, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 246 days.

(21) Appl. No.: 14/726,736

(22) Filed: Jun. 1, 2015

(65) Prior Publication Data

US 2016/0347887 A1    Dec. 1, 2016

(51) Int. Cl.
| | |
|---|---|
| *C08F 210/14* | (2006.01) |
| *C08F 2/01* | (2006.01) |
| *C08F 2/14* | (2006.01) |
| *B01J 19/24* | (2006.01) |
| *G01N 1/20* | (2006.01) |
| *C08F 210/08* | (2006.01) |
| *C08F 10/00* | (2006.01) |
| *C08F 10/02* | (2006.01) |

(52) U.S. Cl.
CPC ......... *C08F 210/14* (2013.01); *B01J 19/2435* (2013.01); *B01J 19/2455* (2013.01); *C08F 2/01* (2013.01); *C08F 2/14* (2013.01); *C08F 210/08* (2013.01); *G01N 1/20* (2013.01); *G01N 1/2035* (2013.01); *B01J 2219/00049* (2013.01); *B01J 2219/24* (2013.01); *C08F 10/00* (2013.01); *C08F 10/02* (2013.01)

(58) Field of Classification Search
CPC ...... G01N 1/2035; B01J 19/2435; C08F 2/01; C08F 2/12

USPC ................... 526/59; 422/68.1, 132; 73/64.56
See application file for complete search history.

(56) References Cited

U.S. PATENT DOCUMENTS

| | | | |
|---|---|---|---|
| 2,825,721 A | 3/1958 | Hogan et al. | |
| 3,119,569 A | 1/1964 | Baricordi | |
| 3,225,023 A | 12/1965 | Hogal et al. | |
| 3,226,205 A | 12/1965 | Rohlfing | |
| 3,242,099 A | 3/1966 | Manyik | |
| 3,248,179 A | 4/1966 | Norwood | |
| 3,556,730 A | 1/1971 | Mitacek | |
| 3,622,521 A | 11/1971 | Hogan et al. | |
| 3,625,864 A | 12/1971 | Horvath | |
| 3,887,494 A | 6/1975 | Dietz | |
| 3,900,457 A | 8/1975 | Witt | |
| 3,976,632 A | 8/1976 | DeLap | |
| 3,999,945 A | 12/1976 | Kushner et al. | |
| 4,053,436 A | 10/1977 | Hogan et al. | |
| 4,081,407 A | 3/1978 | Short et al. | |
| 4,151,122 A | 4/1979 | McDaniel et al. | |

(Continued)

FOREIGN PATENT DOCUMENTS

| | | |
|---|---|---|
| DE | 69124141 T2 | 7/1997 |
| EP | 2030678 | 3/2009 |
| WO | WO 01/09201 | 2/2001 |

OTHER PUBLICATIONS

International Application PCT/US2016/035058 Search Report dated Sep. 9, 2016.

*Primary Examiner* — Fred M Teskin
(74) *Attorney, Agent, or Firm* — Merchant & Gould P.C.

(57) ABSTRACT

Polymerization reactor systems providing integrated liquid-solid sampling systems are disclosed. Methods for operating such polymerization reactor systems and for measuring a property of the liquid portion of liquid-solid mixture are described.

20 Claims, 1 Drawing Sheet

(56) References Cited

U.S. PATENT DOCUMENTS

| | | |
|---|---|---|
| 4,182,815 A | 1/1980 | McDaniel et al. |
| 4,229,971 A | 10/1980 | Ririe, Jr. |
| 4,247,421 A | 1/1981 | McDaniel et al. |
| 4,248,735 A | 2/1981 | McDaniel et al. |
| 4,296,001 A | 10/1981 | Hawley |
| 4,297,460 A | 10/1981 | McDaniel et al. |
| 4,301,034 A | 11/1981 | McDaniel |
| 4,339,559 A | 7/1982 | McDaniel |
| 4,364,842 A | 12/1982 | McDaniel et al. |
| 4,364,854 A | 12/1982 | McDaniel et al. |
| 4,364,855 A | 12/1982 | McDaniel et al. |
| 4,392,990 A | 7/1983 | Witt |
| 4,397,766 A | 8/1983 | Hawley et al. |
| 4,397,769 A | 8/1983 | McDaniel et al. |
| 4,405,501 A | 9/1983 | Witt |
| 4,444,962 A | 4/1984 | McDaniel et al. |
| 4,444,964 A | 4/1984 | McDaniel et al. |
| 4,444,965 A | 4/1984 | McDaniel et al. |
| 4,460,756 A | 7/1984 | McDaniel et al. |
| 4,501,885 A | 2/1985 | Sherk |
| 4,504,638 A | 3/1985 | McDaniel et al. |
| 4,547,557 A | 10/1985 | McDaniel |
| 4,613,484 A | 9/1986 | Ayres et al. |
| 4,735,931 A | 4/1988 | McDaniel et al. |
| 4,806,513 A | 2/1989 | McDaniel et al. |
| 4,808,561 A | 2/1989 | Welborn |
| 4,820,785 A | 4/1989 | McDaniel et al. |
| 4,855,271 A | 8/1989 | McDaniel et al. |
| 4,939,217 A | 7/1990 | Stricklen |
| 4,981,831 A | 1/1991 | Knudsen et al. |
| 4,988,657 A | 1/1991 | Martin et al. |
| 5,037,911 A | 8/1991 | McDaniel et al. |
| 5,179,178 A | 1/1993 | Stacy et al. |
| 5,180,558 A | 1/1993 | Takakarhu |
| 5,191,132 A | 3/1993 | Patsidis et al. |
| 5,210,352 A | 5/1993 | Alt et al. |
| 5,219,817 A | 6/1993 | McDaniel et al. |
| 5,221,654 A | 6/1993 | McDaniel et al. |
| 5,237,025 A | 8/1993 | Benham et al. |
| 5,244,990 A | 9/1993 | Mitchell |
| 5,275,992 A | 1/1994 | Mitchell et al. |
| 5,347,026 A | 9/1994 | Patsidis et al. |
| 5,399,636 A | 3/1995 | Alt et al. |
| 5,401,817 A | 3/1995 | Palackal et al. |
| 5,420,320 A | 5/1995 | Zenk et al. |
| 5,436,305 A | 7/1995 | Alt et al. |
| 5,451,649 A | 9/1995 | Zenk et al. |
| 5,480,848 A | 1/1996 | Geerts |
| 5,496,781 A | 3/1996 | Geerts et al. |
| 5,498,581 A | 3/1996 | Welch et al. |
| 5,541,272 A | 7/1996 | Schmid et al. |
| 5,554,795 A | 9/1996 | Frey et al. |
| 5,563,284 A | 10/1996 | Frey et al. |
| 5,565,175 A | 10/1996 | Hottovy |
| 5,565,592 A | 10/1996 | Patsidis et al. |
| 5,571,880 A | 11/1996 | Alt et al. |
| 5,575,979 A | 11/1996 | Hanson |
| 5,594,078 A | 1/1997 | Welch et al. |
| 5,610,247 A | 3/1997 | Alt et al. |
| 5,627,247 A | 5/1997 | Alt et al. |
| 5,631,203 A | 5/1997 | Welch et al. |
| 5,631,335 A | 5/1997 | Alt et al. |
| 5,654,454 A | 8/1997 | Peifer et al. |
| 5,668,230 A | 9/1997 | Schertl et al. |
| 5,705,478 A | 1/1998 | Boime |
| 5,705,579 A | 1/1998 | Hawley et al. |
| 6,037,184 A | 3/2000 | Matilainen et al. |
| 6,107,230 A | 8/2000 | McDaniel et al. |
| 6,165,929 A | 12/2000 | McDaniel et al. |
| 6,239,235 B1 | 5/2001 | Hottovy |
| 6,262,191 B1 | 7/2001 | Hottovy |
| 6,294,494 B1 | 9/2001 | McDaniel et al. |
| 6,300,271 B1 | 10/2001 | McDaniel |
| 6,316,553 B1 | 11/2001 | McDaniel et al. |
| 6,355,594 B1 | 3/2002 | McDaniel |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel |
| 6,420,497 B1 | 7/2002 | Kufeld et al. |
| 6,524,987 B1 | 2/2003 | Collins et al. |
| 6,548,441 B1 | 4/2003 | McDaniel et al. |
| 6,548,442 B1 | 4/2003 | McDaniel |
| 6,576,583 B1 | 6/2003 | McDaniel et al. |
| 6,613,712 B1 | 9/2003 | McDaniel |
| 6,632,894 B1 | 10/2003 | McDaniel et al. |
| 6,653,416 B2 | 11/2003 | McDaniel et al. |
| 6,667,274 B1 | 12/2003 | Hawley et al. |
| 6,750,302 B1 | 6/2004 | McDaniel et al. |
| 6,831,141 B2 | 12/2004 | McDaniel et al. |
| 6,833,338 B2 | 12/2004 | McDaniel et al. |
| 6,833,415 B2 | 12/2004 | Kendrick |
| 7,026,494 B1 | 4/2006 | Yang et al. |
| 7,041,617 B2 | 5/2006 | Jensen et al. |
| 7,199,073 B2 | 4/2007 | Martin et al. |
| 7,226,886 B2 | 6/2007 | Jayaratne et al. |
| 7,294,599 B2 | 11/2007 | Jensen et al. |
| 7,312,283 B2 | 12/2007 | Martin et al. |
| 7,417,095 B2 | 8/2008 | Battiste |
| 7,417,097 B2 | 8/2008 | Yu et al. |
| 7,517,939 B2 | 4/2009 | Yang et al. |
| 7,601,665 B2 | 10/2009 | McDaniel et al. |
| 7,619,047 B2 | 11/2009 | Yang et al. |
| 7,884,163 B2 | 2/2011 | McDaniel et al. |
| 7,919,639 B2 | 4/2011 | Murray et al. |
| 8,080,681 B2 | 12/2011 | Murray et al. |
| 8,309,485 B2 | 11/2012 | Yang et al. |
| 8,375,772 B2 | 2/2013 | Fukuda et al. |
| 8,475,720 B2 | 7/2013 | Vandaele |
| 8,623,973 B1 | 1/2014 | McDaniel et al. |
| 8,653,206 B2 | 2/2014 | Gessner et al. |
| 8,703,886 B1 | 4/2014 | Yang et al. |
| 8,822,608 B1 | 9/2014 | Bhandarkar et al. |
| 2015/0018503 A1 | 1/2015 | McDaniel et al. |

LIQUID-SOLID SAMPLING SYSTEM FOR A LOOP SLURRY REACTOR

FIELD OF THE INVENTION

The present disclosure concerns methods and systems for the measurement of a property of a liquid in a two-phase liquid-solid mixture, and more particularly relates to the measurement of a property of a liquid in a loop slurry polymerization reactor or similar process.

BACKGROUND OF THE INVENTION

There are various techniques that can be used to separate a liquid stream from a liquid-solid mixture, such as centrifugation, sieving, or flashing. However, these techniques often have drawbacks when rapid and frequent sampling of the liquid stream is required for analytical testing, and excessive waste can be generated. Therefore, it would be beneficial to have a quick and effective liquid-solid separation technique, which does not require centrifugation, sieving, flashing, and the like, yet minimizes the waste generated. Accordingly, it is to these ends that the present disclosure is directed.

SUMMARY OF THE INVENTION

Methods for measuring a property of a liquid in a vessel containing a liquid-solid mixture are disclosed and described herein. In one embodiment of this invention, the method can comprise (i) withdrawing a sample of the liquid-solid mixture from the vessel, (ii) flowing the sample of the liquid-solid mixture through a vertical settling tube, (iii) periodically stopping the flow of the sample of the liquid-solid mixture in the tube for a time period sufficient for the solid to settle to a bottom portion of the tube and for the liquid to occupy an upper portion of the tube, (iv) removing a small fraction of the liquid in the upper portion of the tube and transferring the small fraction of the liquid to an analytical instrument for measuring the property of the liquid, (v) restoring flow through the tube, and (vi) returning an unused fraction of the sample of the liquid-solid mixture to the vessel. While not limited thereto, the vessel can be a loop slurry polymerization reactor.

In another embodiment of this invention, a process for operating a polymerization reactor system is disclosed and described. This process can comprise (I) contacting a transition metal-based catalyst system with an olefin monomer and an optional olefin comonomer in a loop slurry reactor within the polymerization reactor system under polymerization reaction conditions to produce an olefin polymer, the loop slurry reactor containing a liquid-solid mixture, (II) measuring a property of the liquid in the loop slurry reactor, and (III) when the property of the liquid in the loop slurry reactor has reached a predetermined level, adjusting a polymerization reaction condition. The property of the liquid in the loop slurry reactor can be determined by using a method comprising the steps of (i) withdrawing a sample of the liquid-solid mixture from the loop slurry reactor, (ii) flowing the sample of the liquid-solid mixture through a vertical settling tube, (iii) periodically stopping the flow of the sample of the liquid-solid mixture in the tube for a time period sufficient for the solid to settle to a bottom portion of the tube and for the liquid to occupy an upper portion of the tube, (iv) removing a small fraction of the liquid in the upper portion of the tube and transferring the small fraction of the liquid to an analytical instrument for measuring the property of the liquid, (v) restoring flow through the tube, and (vi) returning an unused fraction of the sample of the liquid-solid mixture to the loop slurry reactor.

In yet another embodiment of this invention, a liquid-solid sampling system is disclosed and described. This sampling system can comprise (a) an inlet valve and an inlet pipe for withdrawing a liquid-solid mixture from a vessel, (b) a vertical settling tube downstream of (and connected to) the inlet pipe, the tube configured to segregate the solid to a bottom portion of the tube and for the liquid to occupy an upper portion of the tube (e.g., in the absence of flow), (c) an outlet valve and an outlet pipe for returning an unused fraction of the liquid-solid mixture to the vessel, the outlet pipe downstream of (and connected to) the tube, (d) a sample valve and a sample pipe, the sample valve positioned at the upper portion of the tube and configured to withdraw a small fraction of the liquid in the upper portion of the tube, (e) an analytical instrument downstream of (and connected to) the sample pipe, the analytical instrument configured to measure a property (one or more) of the liquid, and (f) a controller (f1) configured to open the inlet valve and the outlet valve to permit (e.g., continuous) flow of the liquid-solid mixture from the vessel, through the inlet pipe and the tube, and returning to the vessel through the outlet pipe; and (f2) configured to periodically stop flow of the liquid-solid mixture by closing the inlet valve and the outlet valve for a time period sufficient for the solid to settle to the bottom portion of the tube and for the liquid to occupy the upper portion of the tube, and subsequently opening the sample valve to withdraw the small fraction of the liquid from within the upper portion of the tube.

In still another embodiment of this invention, a polymerization reactor system is disclosed and described. This reactor system can comprise (A) a loop slurry reactor configured to contact a transition metal-based catalyst system with an olefin monomer and an optional olefin comonomer under polymerization reaction conditions to produce an olefin polymer, and (B) a liquid-solid sampling system. The liquid-solid sampling system, as provided herein, can comprise (a) an inlet valve and an inlet pipe for withdrawing a liquid-solid mixture from the loop slurry reactor, (b) a vertical settling tube downstream of the inlet pipe, the tube configured to segregate the solid to a bottom portion of the tube and for the liquid to occupy an upper portion of the tube, (c) an outlet valve and an outlet pipe for returning an unused fraction of the liquid-solid mixture to the loop slurry reactor, the outlet pipe downstream of the tube, (d) a sample valve and a sample pipe, the sample valve positioned at the upper portion of the tube and configured to withdraw a small fraction of the liquid in the upper portion of the tube, (e) an analytical instrument downstream of the sample pipe, the analytical instrument configured to measure a property of the liquid, and (f) a controller (f1) configured to open the inlet valve and the outlet valve to permit flow of the liquid-solid mixture from the loop slurry reactor, through the inlet pipe and the tube, and returning to the loop slurry reactor through the outlet pipe; and (f2) configured to periodically stop flow of the liquid-solid mixture by closing the inlet valve and the outlet valve for a time period sufficient for the solid to settle to the bottom portion of the tube and for the liquid to occupy the upper portion of the tube, and subsequently opening the sample valve to withdraw the small fraction of the liquid from within the upper portion of the tube.

Both the foregoing summary and the following detailed description provide examples and are explanatory only. Accordingly, the foregoing summary and the following detailed description should not be considered to be restrictive. Further, features or variations may be provided in addition to those set forth herein. For example, certain embodiments may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claim. A "consisting essentially of" claim occupies a middle ground between closed claims that are written in a "consisting of" format and fully open claims that are drafted in a "comprising" format. Absent an indication to the contrary, for example, describing a compound or composition as "consisting essentially of" is not to be construed as "comprising," but is intended to describe the recited component that includes materials which do not significantly alter the composition or method or system to which the term is applied. For instance, a feedstock consisting essentially of a material A can include impurities typically present in a commercially produced or commercially available sample of the recited compound or composition. When a claim includes different features and/or feature classes (for example, a method step, feedstock features, and/or system features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

Unless otherwise specified, the terms "period" and "periodically" are not intended to be limited to any particular time period, or to have a strictly defined time period associated therewith, and are therefore not limited to uniform, cyclic, or otherwise equal time periods.

In this disclosure, while systems, process, and methods are often described in terms of "comprising" various components, devices, or steps, the systems, processes, and methods can also "consist essentially of" or "consist of" the various components, devices, or steps, unless stated otherwise.

The terms "a," "an," and "the" are intended to include plural alternatives, e.g., at least one. For instance, the disclosure of "a reactor" or "a property" is meant to encompass one, or combinations of more than one, reactor or property, unless otherwise specified.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Various numerical ranges are disclosed herein. When a range of any type is disclosed or claimed herein, the intent is to disclose or claim individually each possible number that such a range could reasonably encompass, including end points of the range as well as any sub-ranges and combinations of sub-ranges encompassed therein, unless otherwise specified. As a representative example, the present application discloses that the polymerization reaction conditions can comprise a polymerization reaction temperature in a range from about 60° C. to about 115° C. in certain embodiments. By a disclosure that the temperature can be in a range from about 60° C. to about 115° C., the intent is to recite that the temperature can be any temperature within the range and, for example, can be equal to about 60° C., about 65° C., about 70° C., about 75° C., about 80° C., about 85° C., about 90° C., about 95° C., about 100° C., about 105° C., about 110° C., or about 115° C. Additionally, the temperature can be within any range from about 60° C. to about 115° C. (for example, the temperature can be in a range from about 70° C. to about 110° C.), and this also includes any combination of ranges between about 60° C. and about 115° C. Likewise, all other ranges disclosed herein should be interpreted in a manner similar to this example.

The term "polymer" is used herein generically to include olefin homopolymers, copolymers, terpolymers, and so forth. A copolymer can be derived from an olefin monomer and one olefin comonomer, while a terpolymer can be derived from an olefin monomer and two olefin comonomers. Accordingly, "polymer" encompasses copolymers and terpolymers derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer could be categorized an as ethylene/1-hexene copolymer. The term "polymer" also is meant to include all molecular weight polymers, and is inclusive of lower molecular weight polymers or oligomers. The term "polymer" as used herein is intended to encompass oligomers (including dimers and trimers) derived from any olefin monomer disclosed herein (as well from an olefin monomer and one olefin comonomer, an olefin monomer and two olefin comonomers, and so forth).

In like manner, the scope of the term "polymerization" includes homopolymerization, copolymerization, and terpolymerization, as well as processes that might also be referred to as oligomerization processes. Therefore, a copolymerization process would involve contacting an olefin monomer (e.g., ethylene) and an olefin comonomer (e.g., 1-hexene) to produce an olefin copolymer.

The terms "contact product," "contacting," and the like, are used herein to describe compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

The term "substantially free of solids," as used herein, means that the sample comprises less than 5 wt. % solids, and often less than 3 wt. % solids, less than 2 wt. % solids, less than 1 wt. % solids, less than 0.5 wt. % solids, or less than 0.1 wt. % solids (or insoluble particulates).

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are methods for determining a property of a liquid in a liquid-solid mixture, and related processes for operating polymerization reactor systems containing a loop slurry reactor. Also disclosed herein are polymerization reactor systems with integrated liquid-solid sampling systems for determining a property of the liquid in the liquid-solid mixture.

While not wishing to be bound by the following theory, it is believed that such reactor systems (and related methods/processes) can provide a quick and effective liquid-solid separation, which does not require centrifugation, sieving, flashing, or any similarly related technique, yet provides a liquid stream that is free or substantially free of solids that might plug or adversely affect analytical equipment. Moreover, only a small fraction of the liquid is extracted for analysis, and the remainder of the liquid-solid mixture is returned to the reactor vessel, thus beneficially reducing the amount of waste generated, particularly the solid waste products. Further, due to the rapid separation and minimal amount of liquid extracted, the frequency of testing can be increased without significantly increasing the waste generated, thus providing more timely data for improved control and consistency of the polymerization process within a reactor system.

Liquid-Solid Sampling Systems and Reactor Systems

Various polymerization reactor systems and liquid-solid sampling systems, and related processes for operating or controlling such systems, are disclosed and described herein. For instance, in one embodiment, a liquid-solid sampling system is provided, and in this embodiment, the sampling system can comprise (a) an inlet valve and an inlet pipe for withdrawing a liquid-solid mixture from a vessel, (b) a vertical settling tube downstream of (and connected to) the inlet pipe, the tube configured to segregate the solid to a bottom portion of the tube and for the liquid to occupy an upper portion of the tube (e.g., in the absence of flow), (c) an outlet valve and outlet pipe for returning an unused fraction of the liquid-solid mixture to the vessel, the outlet pipe downstream of (and connected to) the tube, (d) a sample valve and a sample pipe, the sample valve positioned at the upper portion of the tube and configured to withdraw a small fraction of the liquid in the upper portion of the tube, (e) an analytical instrument downstream of (and connected to) the sample pipe, the analytical instrument configured to measure a property (one or more) of the liquid, and (f) a controller (f1) configured to open the inlet valve and the outlet valve to permit (e.g., continuous) flow of the liquid-solid mixture from the vessel, through the inlet pipe and the tube, and returning to the vessel through the outlet pipe; and (f2) configured to periodically stop flow of the liquid-solid mixture by closing the inlet valve and the outlet valve for a time period sufficient for the solid to settle to the bottom portion of the tube and for the liquid to occupy the upper portion of the tube, and subsequently opening the sample valve to withdraw the small fraction of the liquid from within the upper portion of the tube. Generally, the features of any of the liquid-solid sampling systems disclosed herein (e.g., the vessel, the settling tube, the analytical instrument, the controller configuration, among others) are independently described herein, and these features can be combined in any combination to further describe the disclosed liquid-solid sampling systems. For instance, in some embodiments, the vessel from which the liquid-solid mixture is withdrawn can be a loop slurry reactor. Moreover, other devices or system components can be present in the disclosed sampling systems, unless stated otherwise.

In another embodiment of this invention, a polymerization reactor system is provided, and in this embodiment, the reactor system can comprise (A) a loop slurry reactor (one or more) configured to contact a transition metal-based catalyst system with an olefin monomer and an optional olefin comonomer under polymerization reaction conditions to produce an olefin polymer, and (B) a liquid-solid sampling system. The liquid-solid sampling system, as described herein, can comprise (a) an inlet valve and an inlet pipe for withdrawing a liquid-solid mixture from the loop slurry reactor, (b) a vertical settling tube downstream of the inlet pipe, the tube configured to segregate the solid to a bottom portion of the tube and for the liquid to occupy an upper portion of the tube, (c) an outlet valve and outlet pipe for returning an unused fraction of the liquid-solid mixture to the loop slurry vessel, the outlet pipe downstream of the tube, (d) a sample valve and a sample pipe, the sample valve positioned at the upper portion of the tube and configured to withdraw a small fraction of the liquid in the upper portion of the tube, (e) an analytical instrument downstream of the sample pipe, the analytical instrument configured to measure a property of the liquid, and (f) a controller (f1) configured to open the inlet valve and the outlet valve to permit flow of the liquid-solid mixture from the loop slurry reactor, through the inlet pipe and the tube, and returning to the vessel through the outlet pipe; and (f2) configured to periodically stop flow of the liquid-solid mixture by closing the inlet valve and the outlet valve for a time period sufficient for the solid to settle to the bottom portion of the tube and for the liquid to occupy the upper portion of the tube, and subsequently opening the sample valve to withdraw the small fraction of the liquid from within the upper portion of the tube. Generally, the features of any of the polymerization reactor systems disclosed herein (e.g., the loop slurry reactor, the catalyst system, the olefin monomer (and olefin comonomer, if any), the polymerization conditions, the olefin polymer, the settling tube, the analytical instrument, the controller configuration, among others) are independently described herein, and these features can be combined in any combination to further describe the disclosed polymerization reactor systems. Moreover, other devices or reactor system components can be present in the disclosed polymerization reactor systems, unless stated otherwise. Additionally, the catalyst system can be contacted with an olefin monomer and an olefin comonomer (e.g., contacted with ethylene and an α-olefin comonomer, such as 1-hexene) in the loop slurry reactor in certain embodiments contemplated herein.

In one embodiment, the polymerization reactor system can comprise a single loop slurry reactor, while in another embodiment, the polymerization reactor system can comprise two or more reactors, at least one of which is a loop slurry reactor (e.g., multiple loop slurry reactors, a loop slurry reactor and a gas phase reactor, a loop slurry reactor and a solution reactor, and so forth). Representative slurry polymerization reactors and processes are disclosed, for example, in U.S. Pat. Nos. 3,248,179, 4,501,885, 5,565,175, 5,575,979, 6,239,235, 6,262,191, 6,833,415, and 8,822,608, each of which is incorporated herein by reference in its entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used.

In some embodiments, the polymerization reactor system can comprise any combination of a raw material feed system, a feed system for catalyst and/or catalyst components, and/or a polymer recovery system. In other embodiments, suitable reactor systems can comprise systems for feedstock purification, catalyst storage and preparation, extrusion, reactor cooling, polymer recovery, fractionation, recycle, storage, loadout, laboratory analysis, and process control.

Polymerization conditions that can be monitored, adjusted, and/or controlled for efficiency and to provide desired polymer properties can include, but are not limited to, reactor temperature, reactor pressure, catalyst system flow rate into the reactor, monomer flow rate (and comonomer, if employed) into the reactor, monomer concentration in the reactor, olefin polymer output rate, recycle rate, hydrogen flow rate (if employed), reactor cooling status, and the like. Polymerization temperature can affect catalyst productivity, polymer molecular weight, and molecular weight distribution. A suitable polymerization temperature can be any temperature below the de-polymerization temperature according to the Gibbs Free energy equation. Typically, this includes from about 60° C. to about 280° C., for example, from about 60° C. to about 185° C., from about 60° C. to about 115° C., or from about 130 to about 180° C., depending upon the type of polymerization reactor, the polymer grade, and so forth. In some reactor systems, the polymerization reactor temperature generally can be within a range from about 70° C. to about 110° C., or from about 125° C. to about 175° C.

Suitable pressures will also vary according to the reactor and polymerization type. The pressure for liquid phase polymerizations in a loop reactor typically can be less than 1000 psig (6.89 MPa). The pressure for gas phase polymerization usually can be in the 200 psig to 500 psig range (1.38 MPa to 3.45 MPa). High pressure polymerization in tubular or autoclave reactors generally can be conducted at about 20,000 psig to about 75,000 psig (138 MPa to 517 MPa). Polymerization reactors can also be operated in a supercritical region occurring at generally higher temperatures and pressures. Operation above the critical point of a pressure/temperature diagram (supercritical phase) may offer advantages.

The concentration of the reactants entering the polymerization reactor can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, stereoregularity, crack growth, long chain branching, and rheological measurements.

Embodiments contemplated herein also are directed to, and encompass, the polymers (or oligomers) produced by any of the polymerization reactor systems and processes disclosed herein. Articles of manufacture can be formed from, and/or can comprise, the polymers (or oligomers) produced in accordance with the systems and methods described herein.

Referring now to the liquid-solid sampling system, as described herein, this system can comprise (a) an inlet valve and an inlet pipe for withdrawing a liquid-solid mixture from a vessel. The liquid-solid mixture can take various forms, for instance, a slurry of solids in a liquid diluent. As it pertains to polymerization reactor systems containing a loop slurry reactor, the vessel from which the liquid-solid mixture is withdrawn can be the loop slurry reactor, although not limited thereto. The liquid-solid mixture can be withdrawn from any suitable vessel, device, or location within the polymerization reactor system in which the measurement of a property of the liquid in a two-phase liquid-solid mixture may be beneficial. For example, the inlet valve can be connected to a discharge side of a reactor circulation pump present within the polymerization reactor system. Additionally, the outlet valve can be connected to a suction side of the reactor circulation pump, although not limited thereto. Thus, the unused fraction can be returned to the suction side of the reactor circulation pump.

If desired, the polymerization reactor system can further comprise a diluent flush system configured to prevent plugging of the liquid-solid mixture within the sampling system. The diluent flush system can include, for instance, a vessel containing the diluent and a pump for conveying the diluent. Typically, this diluent flush system can be operated at a pressure higher than that of the vessel (e.g., a loop slurry reactor) from which the liquid-solid sample is withdrawn.

The liquid-solid sampling system, as described herein, can comprise (b) a vertical settling tube downstream of the inlet pipe (i.e., connected to the inlet pipe). The settling tube can be configured to segregate the solid of the liquid-solid mixture to a bottom portion of the settling tube, with the liquid occupying an upper portion of the settling tube. The settling tube is described as a vertical settling tube and, typically, is oriented vertically (within about 5° of the vertical direction), although this is not a requirement. The vertical settling tube can be oriented within about 10° of vertical, within about 20° of vertical, within about 30° of vertical, or within about 45° of vertical, so long as the solids settle to the bottom portion of the settling tube in a suitable period of time. Accordingly, the vertical settling tube generally relies on differences in density between the solid and the liquid (in the liquid-solid mixture) to achieve separation of the liquid from the solid, when there is no flow (or very minimal flow) through the settling tube. Although any suitable density difference between the solid and the liquid can result in separation of the liquid from the solid, quicker and easier separation can be achieved when the density difference is at least 0.1 g/cc, such as at least 0.2 g/cc, at least 0.3 g/cc, or at least 0.5 g/cc, e.g., the density difference can be in a range from about 0.1 g/cc to about 3 g/cc, or from about 0.2 g/cc to about 1 g/cc, and the like.

The specific dimensions, geometric design, and angle of orientation of the settling tube are not particularly limited, and can be adjusted based on the reactor system and liquid-solid mixture of interest. Accordingly, the settling tube can be oriented at any suitable angle, configured with any suitable size and dimension, and can be of any suitable geometric design or shape (e.g., cylinder, cube, sphere, cone, pyramid, or prism) that results in the separation of the liquid from the solid as described herein.

Generally, the vertical settling tube can be configured to operate at a pressure equivalent to that of the vessel (or the loop slurry reactor) from which the liquid-solid mixture is withdrawn, although this is not a requirement. An "equivalent" pressure is meant to encompass pressures within +/−5% of the vessel (or reactor) pressure. For instance, the pressure can be in a range from about 100 psig (0.69 MPa) to about 1000 psig (6.89 MPa), from about 350 psig (2.41 MPa) to about 800 psig (5.52 MPa), or from about 500 psig (3.45 MPa) to about 700 psig (4.83 MPa). Alternatively, the pressure can be less in the vertical settling tube, provided that the lower pressure does not flash or evaporate the liquid component of the liquid-solid mixture while in the settling tube.

The liquid-solid sampling system can comprise (c) an outlet valve and an outlet pipe for returning an unused fraction of the liquid-solid mixture to the vessel. The unused fraction is the portion of the liquid-solid mixture that is not withdrawn for analytical analysis. The outlet pipe is downstream of the vertical settling tube (and connected to the vertical settling tube).

The liquid-solid sampling system can comprise (d) a sample valve and a sample pipe. The sample valve can be positioned at the upper portion of the vertical settling tube and can be configured to withdraw a small fraction of the liquid from within the upper portion of the vertical settling tube. Since the denser solid particles accumulate at the bottom of the vertical settling tube, the sample valve generally is positioned at or near the very top of vertical settling tube, so as to withdraw a sample of the liquid which is substantially free of solids (less than 5 wt. % solids). In some embodiments, the small fraction of the liquid withdrawn from the upper portion of the settling tube contains less than 2 wt. % solids, less than 1 wt. % solids, less than 0.5 wt. % solids, or less than 0.1 wt. % solids, and visually contains no solids or particulates.

Beneficially, the small fraction of the liquid withdrawn from the upper portion of the settling tube is a very minor percentage of the total amount of the liquid-solid mixture in the settling tube. For instance, the small fraction of the liquid removed from the settling tube may be less than 10 mL, less than 5 mL, less than 3 mL, or less than 1 mL. Thus, waste and disposal costs and considerations are minimized. Consistent with embodiments of this invention, the amount of the small fraction of the liquid removed can be less than 5 wt. %, less than 2 wt. %, less than 1 wt. %, or less than 0.5 wt. %, based on the total amount of the liquid-solid mixture in the settling tube.

The liquid-solid sampling system can comprise (e) an analytical instrument downstream of the sample pipe, and connected to the sample pipe. The analytical instrument can be configured to measure a property of the liquid. Any property of the liquid fraction, or combinations of properties of the liquid fraction, in the vessel (or loop slurry reactor) that is useful to know can be measured or determined by the analytical instrument. The analytical instrument is not particularly limited, although the analytical instrument can be a gas chromatograph, a liquid chromatograph, or a spectrometer (e.g., UV spectrometer, IR spectrometer (including a Fourier transform infrared (IR) spectrometer), Raman spectrometer, mass spectrometer, or nuclear magnetic resonance (NMR) spectrometer), or a combination thereof (e.g., a GC-GC Time of Flight (TOF) mass spectrometer (GC-GC TOFMS)), in accordance with certain embodiments of this invention.

Optionally, the liquid-solid sampling system can further comprise a filter assembly located or spaced before the analytical instrument. The filter assembly can filter the small sample fraction of the liquid to remove solids or particulates, if any, prior to analysis by the analytical instrument to determine a property of the liquid. Additionally or alternatively, the liquid-solid sampling system can comprise a carrier gas inlet that enters the sample pipe after the sample valve and before the analytical instrument. Carrier gas, such as any inert gas, from the carrier gas inlet can transfer the small fraction to the analytical instrument.

The liquid-solid sampling system, as described herein, can comprise (f) a controller. The controller can be (f1) configured to open the inlet valve and the outlet valve to permit (e.g., continuous) flow of the liquid-solid mixture from the vessel (or reactor), through the inlet pipe and the vertical settling tube, and returning to the vessel (or reactor) through the outlet pipe. Additionally, the controller can be (f2) configured to periodically stop the flow of the liquid-solid mixture by closing the inlet valve and the outlet valve for a time period sufficient for the solid to settle to the bottom portion of the vertical settling tube and for the liquid to occupy the upper portion of the vertical settling tube, and subsequently opening the sample valve to withdraw the small fraction of the liquid from within the upper portion of the vertical settling tube.

The controller, which can comprise any suitable processing unit or computer system, can be used to control the valve opening and valve closing sequences, for example, to flow the liquid-solid mixture through the settling tube, to extract a sample from the liquid-solid mixture in the settling tube, and so forth, as would be recognized by those of skill in the art. For instance, the controller can perform (f1) continuously for a period of time—e.g., at least 1 min, at least 2 min, at least 5 min, from 1 to 30 min, from 2 to 15 min, or from 3 to 10 min—before (f2) is conducted. Thus, the controller can be configured to conduct sampling on an as-needed basis or at any suitable set time interval, depending upon the requirements of the analytical instrument and the vessel or reactor system.

The controller or computing device can be implemented using a personal computer, a network computer, a server, a mainframe, or other similar microcomputer-based workstation. The controller or computing device can comprise any computer operating environment, such as hand-held devices, multiprocessor systems, microprocessor-based or programmable sender electronic devices, minicomputers, mainframe computers, and the like. The controller or computing device also can be practiced in distributed computing environments where tasks are performed by remote processing devices. Furthermore, the controller or computing device can comprise a mobile terminal, such as a smart phone, a cellular telephone, a cellular telephone utilizing wireless application protocol (WAP), personal digital assistant (PDA), intelligent pager, portable computer, a hand held computer, a conventional telephone, a wireless fidelity (Wi-Fi) access point, or a facsimile machine. The aforementioned systems and devices are examples, and the controller or computing device can comprise other systems or devices. Controller or computing device also can be implemented via a system-on-a-chip (SOC) where each and/or many of the components illustrated above can be integrated onto a single integrated circuit. Such an SOC device can include one or more processing units, graphics units, communications units, system virtualization units and various application functionalities, all of which can be integrated (or "burned") onto the chip substrate as a single integrated circuit. Other controller methodologies and devices are readily apparent to one of skill in the art in view of this disclosure.

In some embodiments, a beneficial aspect of the liquid-solid sampling systems and polymerization reactor systems is that these systems do not require a typical liquid-solid separation device, such as a centrifuge, a flash drum, or a sieve, in order to produce a liquid fraction for analysis that is substantially free of any solids or particulates.

Figure 1:
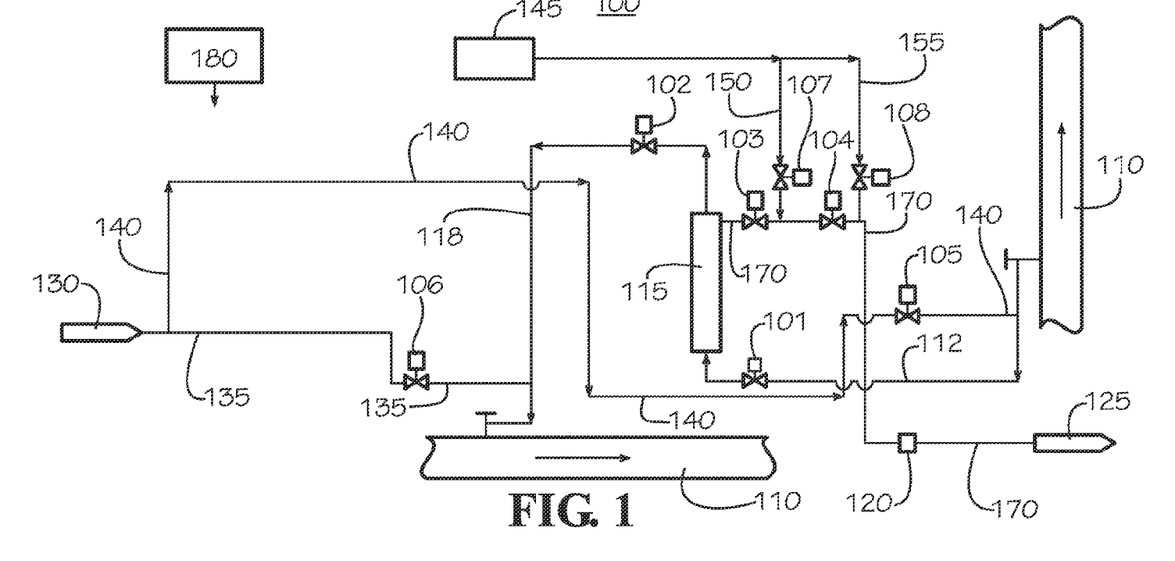
FIG. 1 illustrates a schematic flow diagram of a polymerization reactor system, with an integrated liquid-solid sampling system, consistent with embodiments of this disclosure.

A representative polymerization reactor system 100, with an integrated liquid-solid sampling system, consistent with embodiments of this invention is illustrated in FIG. 1. The polymerization reactor system 100 includes a reactor vessel 110, a settling tube 115, an analytical instrument 125, a diluent flush system 130, a carrier gas system 145, and a controller 180. For emphasis on the features of the sampling system, the reactor vessel 110 is shown only as partial sections of a loop slurry reactor, with the flow direction indicated by the arrows. An inlet valve 101 and an inlet pipe 112 (for withdrawing a sample of the liquid-solid mixture from the reactor vessel 110) are connected to the reactor vessel 110 at a location different from an outlet valve 102 and an outlet pipe 118 (for returning the unused fraction of the liquid-solid mixture to the reactor vessel 110), although this is not a requirement. The diluent flush system 130 can have a first diluent flush line 140 and a second diluent flush line 135. The first diluent flush line 140 is connected to the inlet pipe 112 and prevents plugging of the liquid-solid mixture, and the flow of the diluent in the first diluent flush line 140 is regulated by a first diluent flush valve 105. The second diluent flush line 135 is connected to the outlet pipe 118 and prevents plugging of the liquid-solid mixture, and the flow of the diluent in the second diluent flush line 135 is regulated by a second diluent flush valve 106.

The sample of the liquid-solid mixture from the reactor vessel 110 flows from the inlet pipe 112 into the settling tube 115, which is oriented vertically, and the unused fraction returns to the reactor vessel 100 via the outlet pipe 118. At or near the top of the settling tube 115 is a sample pipe 170 and a sample valve 103, which serve to withdraw a small fraction of the liquid from the upper portion of the settling tube 115. The liquid sample in the sample pipe 170 proceeds to an in-line filter 120 and then to the analytical instrument 125 for measurement of at least one property of the liquid portion of the liquid-solid mixture. At any point in the sample pipe 170, the liquid sample from the settling tube 115 may be converted to the gas phase by one or more of increased temperature and reduced pressure, or by any other suitable means.

The carrier gas system 145 can have a first carrier gas line 150 (with flow controlled by a first carrier gas valve 107) and a second carrier gas line 155 (with flow controlled by a second carrier gas valve 108). Any suitable inert gas can be used in the carrier gas system 145. A sample sweep valve 104 is positioned on the sample pipe 170 between the entry points of the first carrier gas line 150 and the second carrier gas line 155 on the sample pipe 170. As described further hereinbelow, by appropriately sequencing the sample valve 103, the sample sweep valve 104, the first carrier gas valve 107, and the second carrier gas valve 108, a small fraction of the liquid from the upper portion of the settling tube 115 can be withdrawn, and then subsequently carried through the sample pipe 170 to the analytical instrument 125 for any suitable measurement or analysis.

In FIG. 1, the controller 180 is illustrated with an arrow pointing down to indicate that the controller acts on or controls certain aspects of the polymerization reactor system 100. In particular, as shown representatively in FIG. 2, the controller 180 acts on or controls each of the inlet valve 101, the outlet valve 102, the sample valve 103, the sample sweep valve 104, the first diluent flush valve 105, the second diluent flush valve 106, the first carrier gas valve 107, and the second carrier gas valve 108. The controller 180 opens or closes the respective valves in certain orders or predetermined sequences in order to withdraw a liquid-solid mixture sample from the reactor vessel 110, in order to withdraw a small liquid fraction from the settling tube 115, in order to sweep the liquid fraction to the analytical instrument 125 for analysis, and so forth.

Measurement Methods for a Liquid-Solid Mixture

Embodiments of this invention are directed to methods for measuring a property of a liquid in a vessel containing a liquid-solid mixture. Such methods can comprise (or consist essentially of, or consist of) (i) withdrawing a sample of the liquid-solid mixture from the vessel, (ii) flowing the sample of the liquid-solid mixture through a vertical settling tube, (iii) periodically stopping the flow of the sample of the liquid-solid mixture in the vertical settling tube for a time period sufficient for the solid to settle to a bottom portion of the vertical settling tube and for the liquid to occupy an upper portion of the vertical settling tube, (iv) removing a small fraction of the liquid in the upper portion of the vertical settling tube and transferring the small fraction of the liquid to an analytical instrument for measuring the property of the liquid, (v) restoring flow through the vertical settling tube, and (vi) returning an unused fraction of the sample of the liquid-solid mixture to the vessel. Generally, the features of the methods disclosed herein (e.g., the vessel, the settling tube, the analytical instrument, among others) are independently described herein, and these features can be combined in any combination to further describe the disclosed methods. For instance, the vessel from which the liquid-solid mixture is withdrawn can be a loop slurry reactor. Moreover, other process steps can be conducted before, during, and/or after any of the steps listed in the disclosed methods, unless stated otherwise.

Embodiments of this invention also are directed to processes for operating polymerization reactor systems. Such processes can comprise (I) contacting a transition metal-based catalyst system with an olefin monomer and an optional olefin comonomer in a loop slurry reactor within the polymerization reactor system under polymerization reaction conditions to produce an olefin polymer, the loop slurry reactor containing a liquid-solid mixture, (II) measuring a property of the liquid in the loop slurry reactor, and (III) when the property of the liquid in the loop slurry reactor has reached a predetermined level, adjusting a polymerization reaction condition. The property of the liquid in the loop slurry reactor can be determined by using a method comprising the steps of (i) withdrawing a sample of the liquid-solid mixture from the loop slurry reactor, (ii) flowing the sample of the liquid-solid mixture through a vertical settling tube, (iii) periodically stopping the flow of the sample of the liquid-solid mixture in the vertical settling tube for a time period sufficient for the solid to settle to a bottom portion of the vertical settling tube and for the liquid to occupy an upper portion of the vertical settling tube, (iv) removing a small fraction of the liquid in the upper portion of the vertical settling tube and transferring the small fraction of the liquid to an analytical instrument for measuring the property of the liquid, (v) restoring flow through the vertical settling tube, and (vi) returning an unused fraction of the sample of the liquid-solid mixture to the loop slurry reactor. Generally, the features of the processes disclosed herein (e.g., the loop slurry reactor, the catalyst system, the olefin monomer (and olefin comonomer, if any), the polymerization conditions, the olefin polymer, the settling tube, the analytical instrument, among others) are independently described herein, and these features can be combined in any combination to further describe the disclosed processes. Moreover, other process steps can be conducted before, during, and/or after any of the steps listed in the disclosed processes, unless stated otherwise.

In step (i), a sample of the liquid-solid mixture can be withdrawn from the vessel (or loop slurry reactor). The sample can be withdrawn periodically, or a continuous sample can be withdrawn. This withdrawn sample flows through the vertical settling tube in step (ii). This step can be performed for any suitable length of time before step (iii) is conducted, such as continuously for at least 1 min, at least 2 min, or at least 5 min, or continuously for from 1 to 30 min, from 2 to 15 min, or from 3 to 10 min. Periodically, in step (iii), the flow of the sample of the liquid-solid mixture in the vertical settling tube is stopped for a time period sufficient for the solid to settle to a bottom portion of the vertical settling tube and for the liquid to occupy an upper portion of the vertical settling tube. Any suitable time period can be used for the solid to begin to settle, and this can depend upon, for example, the density difference between that of the liquid and the solid. Additionally, the time period should not be excessive so as to cause plugging within the liquid-solid sampling system. In some embodiments, the time period used can be from about 1 sec to about 5 min, from about 1 sec to about 1 min, from about 5 sec to about 1 min, from about 10 sec to about 45 sec, from about 15 sec to about 2 min, or from about 30 sec to about 90 sec, and the like.

In step (iv), a small fraction of the liquid in the upper portion of the vertical settling tube can be extracted and transferred to an analytical instrument for measuring any desired property of the liquid. During the step of transferring the small fraction of the liquid, the liquid can be vaporized, such as by increasing temperature, decreasing pressure, or other suitable technique. Further, a carrier gas (e.g., an inert gas) can be used to facilitate the transfer of the small fraction of the liquid from the vertical sampling tube to the analytical instrument.

The analytical instrument (and, therefore, the property of the liquid being measured) is not particularly limited. Generally, however, the analytical instrument can be a gas chromatograph, a liquid chromatograph, a mass spectrometer, a UV spectrometer, an infrared spectrometer, a Raman spectrometer, a Fourier transform infrared spectrometer, a nuclear magnetic resonance (NMR) spectrometer, and the like, as well as combinations thereof (e.g., a GC-GC Time of Flight (TOF) mass spectrometer (GC-GC TOFMS)). If desired, the liquid extracted from the vertical settling tube can be filtered prior to the analytical instrument.

After the small fraction of the liquid has been extracted for analysis, in steps (v) and (vi), the flow is restored through the vertical settling tube, and the unused fraction of the sample of the liquid-solid mixture (minus the small fraction of the liquid that was extracted) can be returned to the vessel (or loop slurry reactor). Beneficially, this technique minimizes the amount of waste generated, since only the small fraction analyzed by the analytical instrument is disposed of.

Also beneficially, the methods and processes disclosed herein do not require a typical liquid-solid separation step, such as centrifuging, a flashing, or sieving, in order to adequately separate the solids from the liquid, in order produce a liquid fraction for analysis that is substantially free of any solids or particulates.

In some embodiments, at least one of step (i) thru step (vi) is conducted at a pressure equivalent to vessel (or reactor) pressure, while in other embodiments, all of steps (i) thru (vi) are conducted at a pressure equivalent to vessel (or reactor) pressure. In these embodiments, "equivalent" pressure is meant to encompass pressures within +/−5% of the vessel (or reactor) pressure. While not limited thereto, the pressure can be in a range from about 100 psig (0.69 MPa) to about 1000 psig (6.89 MPa), from about 350 psig (2.41 MPa) to about 800 psig (5.52 MPa), or from about 500 psig (3.45 MPa) to about 700 psig (4.83 MPa), in certain embodiments of this invention.

Consistent with particular embodiments of this invention, the sample of the liquid-solid mixture withdrawn from the loop slurry reactor, in step (i), can be withdrawn from a discharge side of a reactor circulation pump present within the polymerization reactor system. Additionally or alternatively, the unused fraction of the liquid-solid mixture, in step (vi), can be returned to a suction side of the reactor circulation pump, although not limited thereto. If desired, flushes of a diluent can be used in to prevent plugging of the liquid-solid mixture within the sampling system.

The methods disclosed herein are applicable to a wide variety of circumstances where a loop slurry reactor (containing a liquid-solid mixture) is employed, and a property of the liquid in the loop slurry reactor may be of interest. For example, the amount of monomer present in the liquid, the amount of comonomer present in the liquid, the amount of hydrogen present in the liquid, the amount of any catalyst system component present in the liquid, the amount of olefin polymer product in the liquid, and the like, may be of interest. Consistent with embodiments disclosed herein, when the property of the liquid (e.g., an amount of any particular material in the liquid) has reached a predetermined level, a polymerization reaction condition can be adjusted. The predetermined level can be ascertained by one of skill in the art depending upon, for instance, the historic and the prevailing conditions in the polymerization reactor system. As non-limiting examples, a predetermined level may be a decrease of a certain percentage (e.g., above a percentage that is deemed allowable during normal on-prime production) or the increase of a certain percentage of the amount of any particular material present in the liquid. For instance, if the monomer concentration in the liquid is too low, then the feed rate of the monomer to the polymerization reactor system (e.g., to the loop reactor) can be increased to bring the monomer concentration to an acceptable level. As another example, if the polymer concentration in the liquid is too high, then the reaction temperature can be decreased (to decrease solubility) to bring the polymer concentration to an acceptable level.

Catalyst Systems

The methods, processes, and reactor systems disclosed herein are applicable to any catalyst system (e.g., any transition metal-based catalyst system) suitable for the polymerization of an olefin monomer, but are not limited thereto. The catalyst system can comprise, for example, a transition metal (one or more than one) from Groups IIIB-XB of the Periodic Table of the Elements. In one embodiment, the catalyst system can comprise a Group III, IV, V, or VI transition metal, or a combination of two or more transition metals. The catalyst system can comprise chromium, titanium, zirconium, hafnium, vanadium, or a combination thereof, in some embodiments, or can comprise chromium, titanium, zirconium, hafnium, or a combination thereof, in other embodiments. Accordingly, the catalyst system can comprise chromium, or titanium, or zirconium, or hafnium, either singly or in combination. Thus, catalyst systems comprising two or more transition metal compounds, wherein each transition metal compound independently can comprise chromium, titanium, zirconium, hafnium, vanadium, or a combination thereof, are contemplated and encompassed herein.

Various catalyst systems known to a skilled artisan are useful in the polymerization of olefins. These include, but are not limited to, Ziegler-Natta based catalyst systems, chromium-based catalyst systems, metallocene-based catalyst systems, and the like, including combinations thereof. The polymerization processes and reactor systems disclosed herein are not limited to the aforementioned catalyst systems, but Applicants nevertheless contemplate particular embodiments directed to these catalyst systems. Hence, the catalyst system can be a Ziegler-Natta based catalyst system, a chromium-based catalyst system, and/or a metallocene-based catalyst system; alternatively, a Ziegler-Natta based catalyst system; alternatively, a chromium-based catalyst system; or alternatively, a metallocene-based catalyst system. In one embodiment, the catalyst system can be a dual catalyst system comprising at least one metallocene compound, while in another embodiment, the catalyst system can be a dual catalyst system comprising two different metallocene compounds.

Examples of representative and non-limiting catalyst systems include those disclosed in the U.S. Pat. Nos. 3,887,494, 3,119,569, 4,053,436, 4,981,831, 4,364,842, 4,444,965, 4,364,855, 4,504,638, 4,364,854, 4,444,964, 4,444,962, 3,976,632, 4,248,735, 4,297,460, 4,397,766, 2,825,721, 3,225,023, 3,226,205, 3,622,521, 3,625,864, 3,900,457, 4,301,034, 4,547,557, 4,339,559, 4,806,513, 5,037,911, 5,219,817, 5,221,654, 4,081,407, 4,296,001, 4,392,990, 4,405,501, 4,151,122, 4,247,421, 4,397,769, 4,460,756, 4,182,815, 4,735,931, 4,820,785, 4,988,657, 5,436,305, 5,610,247, 5,627,247, 3,242,099, 4,808,561, 5,275,992, 5,237,025, 5,244,990, 5,179,178, 4,855,271, 4,939,217, 5,210,352, 5,401,817, 5,631,335, 5,571,880, 5,191,132, 5,480,848, 5,399,636, 5,565,592, 5,347,026, 5,594,078, 5,498,581, 5,496,781, 5,563,284, 5,554,795, 5,420,320, 5,451,649, 5,541,272, 5,705,478, 5,631,203, 5,654,454, 5,705,579, 5,668,230, 6,300,271, 6,831,141, 6,653,416, 6,613,712, 7,294,599, 6,355,594, 6,395,666, 6,833,338, 7,417,097, 6,548,442, 7,312,283, 7,026,494, 7,041,617, 7,199,073, 7,226,886, 7,517,939, 7,619,047, 7,919,639, and 8,080,681, each of which is incorporated herein by reference in its entirety.

In some embodiments, the catalyst system, in addition to a transition metal compound, can contain an activator and an optional co-catalyst. Illustrative activators can include, but are not limited to, aluminoxane compounds, organoboron or organoborate compounds, ionizing ionic compounds, activator-supports (e.g., solid oxides treated with an electron-withdrawing anion), and the like, or combinations thereof. Commonly used polymerization co-catalysts can include, but are not limited to, metal alkyl, or organometal, co-catalysts, with the metal encompassing boron, aluminum, and the like. For instance, alkyl boron and/or alkyl aluminum compounds often can be used as co-catalysts in a transition metal-based catalyst system. Representative compounds can include, but are not limited to, tri-n-butyl borane, tripropylborane, triethylborane, trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, including combinations thereof. In these and other embodiments, the transition metal compound can comprise a metallocene compound and/or a chromium compound. The metallocene compound can be a bridged metallocene or an unbridged metallocene compound.

In some embodiments, the transition metal-based catalyst system can comprise (or consist essentially of, or consist of) a transition metal supported on, impregnated onto, and/or mixed or cogelled with a carrier. The transition metal compound, whether a metallocene compound, chromium compound, or other, can be supported on, impregnated onto, and/or mixed or cogelled with any of a number of porous carriers including, but not limited to, solid oxides, activator-supports (chemically-treated solid oxides), molecular sieves and zeolites, clays and pillared clays, and the like. For example, the transition metal-based catalyst system can comprise chromium impregnated onto silica, chromium impregnated onto silica-titania, chromium impregnated onto aluminophosphate, chromium cogelled with silica, chromium cogelled with silica-titania, or chromium cogelled with aluminophosphate, and this includes any combinations of these materials.

Solid Oxides

In some embodiments, the transition metal-based catalyst system can contain a solid oxide. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: *Hawley's Condensed Chemical Dictionary*, 11$^{th}$ Ed., John Wiley & Sons, 1995; Cotton, F. A., Wilkinson, G., Murillo, C. A., and Bochmann, M., *Advanced Inorganic Chemistry*, 6$^{th}$ Ed., Wiley-Interscience, 1999). For example, the solid inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used as components of a catalyst system can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof.

The solid oxide can encompass oxide materials such as alumina, "mixed oxide" compounds thereof such as silica-alumina, and combinations or mixtures of more than one solid oxide material. Mixed oxides such as silica-alumina can be single or multiple chemical phases with more than one metal combined with oxygen to form the solid oxide. Examples of mixed oxides that can be used herein include, but are not limited to, silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, and the like, or a combination thereof. Silica-coated aluminas are encompassed herein; such oxide materials are described in, for example, U.S. Pat. No. 7,884,163, the disclosure of which is incorporated herein by reference in its entirety.

The percentage of each oxide in a mixed oxide can vary depending upon the respective oxide materials. As an example, a silica-alumina typically has an alumina content from 5% to 95% by weight. According to one embodiment, the alumina content of the silica-alumina can be from 5% to 50% alumina by weight, or from 8% to 30% alumina by weight. In another embodiment, high alumina content silica-alumina compounds can be employed, in which the alumina content of these silica-alumina materials typically ranges from 60% to 90% alumina by weight, or from 65% to 80% alumina by weight.

In one embodiment, the solid oxide can comprise silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof; alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another embodiment, the solid oxide can comprise silica, alumina, titania, zirconia, magnesia, boria, zinc oxide, a mixed oxide thereof, or any mixture thereof. For instance, the solid oxide can comprise silica, alumina, titania, or a combination thereof alternatively, silica; alternatively, alumina; alternatively, titania; alternatively, zirconia; alternatively, magnesia; alternatively, boria; or alternatively, zinc oxide.

In some embodiments, the solid oxide can have a pore volume greater than 0.1 cc/g, or alternatively, greater than 0.5 cc/g. Often, the solid oxide can have a pore volume greater than 1.0 cc/g. Additionally, or alternatively, the solid oxide can have a surface area greater than 100 m$^2$/g; alternatively, greater than 250 m$^2$/g; or alternatively, greater than 350 m$^2$/g. For example, the solid oxide can have a surface area of from 100 m$^2$/g to 1000 m$^2$/g, from 200 m$^2$/g to 800 m$^2$/g, or from 250 m$^2$/g to 600 m$^2$/g.

Activator-Supports

The present invention encompasses various transition metal-based catalyst systems which can contain an activator-support. In one embodiment, the activator-support can comprise a solid oxide treated with an electron-withdrawing anion. Alternatively, in another embodiment, the activator-support can comprise a solid oxide treated with an electron-withdrawing anion, the solid oxide containing a Lewis-acidic metal ion. Non-limiting examples of suitable activator-supports are disclosed in, for instance, U.S. Pat. Nos. 7,294,599, 7,601,665, 7,884,163, 8,309,485, 8,623,973, and 8,703,886, and U.S. Patent Publication No. 2015/0018503, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form an activator-support, either singly or in combination, can include, but are not limited to, silica-alumina, silica-titania, silica-zirconia, alumina-titania, alumina-zirconia, zinc-aluminate, alumina-boria, silica-boria, aluminophosphate-silica, titania-zirconia, and the like. The solid oxide used herein also can encompass oxide materials such as silica-coated alumina, as described in U.S. Pat. No. 7,884,163.

Accordingly, in one embodiment, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another embodiment, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another embodiment, the solid oxide can comprise silica, alumina, titania, zirconia, magnesia, boria, zinc oxide, any mixed oxide thereof, or any combination thereof. In yet another embodiment, the solid oxide can comprise silica-alumina, silica-coated alumina, silica-titania, silica-zirconia, alumina-boria, or any combination thereof. In still another embodiment, the solid oxide can comprise alumina, silica-alumina, silica-coated alumina, or any mixture thereof; alternatively, alumina; alternatively, silica-alumina; or alternatively, silica-coated alumina.

The silica-alumina or silica-coated alumina solid oxide materials which can be used can have an silica content from about 5 to about 95% by weight. In one embodiment, the silica content of these solid oxides can be from about 10% to about 80% silica by weight, or from about 20% to about 70% silica by weight. In another embodiment, such materials can have silica contents ranging from about 15% to about 60% silica by weight, or from about 25% to about 50% silica by weight. The solid oxides contemplated herein can have any suitable surface area, pore volume, and particle size, as would be recognized by those of skill in the art.

The electron-withdrawing component used to treat the solid oxide can be any component that increases the Lewis or Bronsted acidity of the solid oxide upon treatment (as compared to the solid oxide that is not treated with at least one electron-withdrawing anion). According to one embodiment, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, and the like, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, and the like, or any combination thereof, in some embodiments provided herein. In other embodiments, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other embodiments, the electron-withdrawing anion can comprise fluoride and/or sulfate.

The activator-support generally can contain from about 1 wt. % to about 25 wt. % of the electron-withdrawing anion, based on the weight of the activator-support. In particular embodiments provided herein, the activator-support can contain from about 1 wt. % to about 20 wt. %, from about 2 wt. % to about 20 wt. %, from about 3 wt. % to about 20 wt. %, from about 2 wt. % to about 15 wt. %, from about 3 wt. % to about 15 wt. %, from about 3 wt. % to about 12 wt. %, or from about 4 wt. % to about 10 wt. %, of the electron-withdrawing anion, based on the total weight of the activator-support.

In an embodiment, the activator-support can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof. In another embodiment, the activator-support employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. In yet another embodiment, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some embodiments, the activator-support can comprise a fluorided solid oxide, while in other embodiments, the activator-support can comprise a sulfated solid oxide.

Various processes can be used to form activator-supports useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, and the like, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing activator-supports (e.g., fluorided solid oxides, sulfated solid oxides, or phosphated solid oxides) are well known to those of skill in the art.

Olefin Monomers and Polymers

Olefin monomers contemplated herein typically include olefin compounds having from 2 to 30 carbon atoms per molecule and having at least one olefinic double bond. Homopolymerization processes using a single olefin, such as ethylene, propylene, butene, hexene, octene, and the like, are encompassed, as well as copolymerization and terpolymerization reactions using an olefin monomer with at least one different olefinic compound. As previously disclosed, polymerization processes are meant to encompass oligomerization processes as well.

As an example, any resultant ethylene copolymers and terpolymers generally can contain a major amount of ethylene (>50 mole percent) and a minor amount of comonomer (<50 mole percent). Comonomers that can be copolymerized with ethylene often have from 3 to 20 carbon atoms in their molecular chain.

Acyclic, cyclic, polycyclic, terminal (α), internal, linear, branched, substituted, unsubstituted, functionalized, and non-functionalized olefins can be employed. For example, typical unsaturated compounds that can be polymerized to produce olefin polymers can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described herein. Styrene also can be employed as a monomer or as a comonomer. In an embodiment, the olefin monomer can comprise a $C_2$-$C_{24}$ olefin; alternatively, a $C_2$-$C_{12}$ olefin; alternatively, a $C_6$-$C_{24}$ olefin; alternatively, a $C_2$-$C_{10}$ α-olefin; alternatively, propylene, 1-butene, 1-pentene, 1-hexene, 1-heptene, 1-octene, 1-decene, or styrene; alternatively, ethylene, propylene, 1-butene, 1-hexene, or 1-octene; alternatively, ethylene or propylene; alternatively, ethylene; or alternatively, propylene.

When a copolymer (or alternatively, a terpolymer) is desired, the olefin monomer can comprise, for example, ethylene or propylene, which is copolymerized with at least one comonomer. According to one embodiment, the olefin monomer in the polymerization process can comprise ethylene. In this embodiment, examples of suitable olefin comonomers can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to another embodiment, the olefin monomer can comprise ethylene and the olefin comonomer can comprise an a-olefin, while in yet another embodiment, the comonomer can comprise propylene, 1-butene, 1-pentene, 1-hexene, 1-octene, 1-decene, styrene, or any combination thereof; or alternatively, the olefin comonomer can comprise 1-butene, 1-hexene, 1-octene, or a combination thereof.

Generally, the amount of comonomer introduced into a polymerization reactor to produce the copolymer can be from about 0.01 weight percent to about 50 weight percent of the comonomer based on the total weight of the monomer and comonomer. According to another embodiment, the amount of comonomer introduced into a polymerization reactor can be from about 0.01 weight percent to about 40 weight percent comonomer based on the total weight of the monomer and comonomer. In still another embodiment, the amount of comonomer introduced into a polymerization reactor can be from about 0.1 weight percent to about 35 weight percent comonomer based on the total weight of the monomer and comonomer. Yet, in another embodiment, the amount of comonomer introduced into a polymerization reactor can be from about 0.5 weight percent to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization reaction. Thus, branched and/or cyclic portion(s) of the olefin removed somewhat from the carbon-carbon double bond would not be expected to hinder the reaction in the way that the same olefin substituents situated more proximate to the carbon-carbon double bond might.

According to one embodiment, at least one monomer/reactant can be ethylene, so the polymerization reaction can be a homopolymerization involving only ethylene, or a copolymerization with a different acyclic, cyclic, terminal, internal, linear, branched, substituted, or unsubstituted olefin. In addition, the methods disclosed herein intend for olefin to also encompass diolefin compounds that include, but are not limited to, 1,3-butadiene, isoprene, 1,4-pentadiene, 1,5-hexadiene, and the like.

Olefin polymers encompassed herein can include any polymer (or oligomer) produced from any olefin monomer (and optional comonomer(s)) described herein. For example, the olefin polymer can comprise an ethylene homopolymer, a propylene homopolymer, an ethylene copolymer (e.g., ethylene/1-butene, ethylene/1-hexene, or ethylene/1-octene), a propylene random copolymer, a propylene block copolymer, and the like, including combinations thereof. Moreover, the olefin polymer (or oligomer) can comprise, in certain embodiments, an olefin dimer, olefin trimer, or olefin tetramer, and including mixtures or combinations thereof. Thus, olefin polymer encompasses oligomerization products of $C_6$-$C_{24}$ olefins (or $C_6$-$C_{24}$ α-olefins, or 1-hexene, or 1-octene, or 1-decene, or 1-dodecene, or 1-tetradecene, or 1-hexadecene).

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

Figure 2:
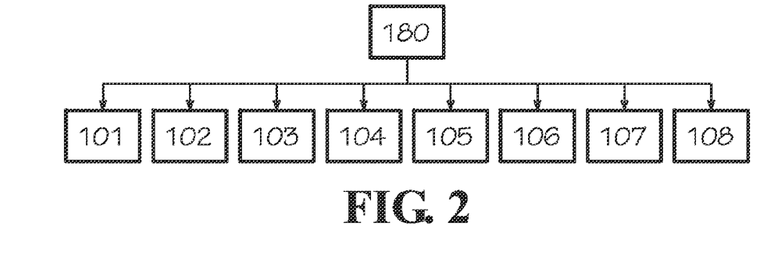
FIG. 2 illustrates a general representation of a control scheme in accordance with embodiments of the present disclosure, with a controller acting on the valves of FIG. 1.

These examples are provided to demonstrate the control and implementation of a liquid-solid sampling system, as part of a polymerization reactor system, in reference to FIGS. 1-2. A first valve protocol is for when no sample is being sent to the analytical instrument for analysis. In this first protocol, the inlet valve 101 and the outlet valve 102 are opened (allowing continuous flow of the liquid-solid mixture from the reactor vessel, through the settling tube, and back to the reactor vessel), and the sample sweep valve 104 and the second carrier gas valve 108 are opened, while the other valves are closed.

A second valve protocol is for liquid-solid settling in the settling tube. In this second protocol, the inlet valve 101 and the outlet valve 102 are closed, as is the sample valve 103, for a period of time sufficient for the solids to move to the bottom of the settling tube (due to their higher density), resulting in liquid at the top of the settling tube.

A third valve protocol is for the extraction of the liquid sample from the top of the settling tube. In this third protocol, the inlet valve 101 and the outlet valve 102 remain closed, but the sample valve 103 is opened. However, the sample sweep valve 104 and the first carrier gas valve 107 are closed.

A fourth valve protocol is for transferring the sample to the analytical instrument for analysis. In this fourth protocol, the inlet valve 101 and the outlet valve 102 are opened, again permitting continuous flow of the liquid-solid mixture from the reactor vessel, through the settling tube, and back to the reactor vessel. The sample valve 103 is closed, and the sample sweep valve 104 and the first carrier gas valve 107 are opened, transferring the extracted sample to the analytical instrument.

A fifth valve protocol is a return to the condition where no sample is being sent to the analytical instrument for analysis. In this fifth protocol, the inlet valve 101, the outlet valve 102, the sample sweep valve 104, and the second carrier gas valve 108 are opened, while the other valves are closed. Table I provides a summary of these valve protocols in an order or sequence typically utilized in a polymerization reactor system containing a liquid-solid sampling system.

TABLE I

| Valve Number | 101 | 102 | 103 | 104 | 105 | 106 | 107 | 108 |
|---|---|---|---|---|---|---|---|---|
| No sample for analysis | Open | Open | Close | Open | Close | Close | Close | Open |
| Liquid-solid settling | Close | Close | Close | Open | Open | Open | Close | Open |
| Liquid sample extracted | Close | Close | Open | Close | Open | Open | Close | Open |
| Sample sweep for analysis | Open | Open | Close | Open | Close | Close | Open | Close |
| No sample for analysis | Open | Open | Close | Open | Close | Close | Close | Open |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments typically are described as "comprising" but, alternatively, can "consist essentially of" or "consist of" unless specifically stated otherwise):

Embodiment 1. A method for measuring a property of a liquid in a vessel containing a liquid-solid mixture, the method comprising:
(i) withdrawing a sample of the liquid-solid mixture from the vessel;
(ii) flowing the sample of the liquid-solid mixture through a vertical settling tube;
(iii) periodically stopping the flow of the sample of the liquid-solid mixture in the tube for a time period sufficient for the solid to settle to a bottom portion of the tube and for the liquid to occupy an upper portion of the tube;
(iv) removing a small fraction of the liquid in the upper portion of the tube and transferring the small fraction of the liquid to an analytical instrument for measuring the property of the liquid;
(v) restoring flow through the tube; and
(vi) returning an unused fraction of the sample of the liquid-solid mixture to the vessel.

Embodiment 2. The method defined in embodiment 1, wherein the vessel is a loop slurry reactor.

Embodiment 3. A process for operating a polymerization reactor system, the process comprising:
(I) contacting a transition metal-based catalyst system with an olefin monomer and an optional olefin comonomer in a loop slurry reactor within the polymerization reactor system under polymerization reaction conditions to produce an olefin polymer, the loop slurry reactor containing a liquid-solid mixture;
(II) measuring a property of the liquid in the loop slurry reactor via a method comprising the steps of:
  (i) withdrawing a sample of the liquid-solid mixture from the loop slurry reactor;
  (ii) flowing the sample of the liquid-solid mixture through a vertical settling tube;
  (iii) periodically stopping the flow of the sample of the liquid-solid mixture in the tube for a time period sufficient for the solid to settle to a bottom portion of the tube and for the liquid to occupy an upper portion of the tube;
  (iv) removing a small fraction of the liquid in the upper portion of the tube and transferring the small fraction of the liquid to an analytical instrument for measuring the property of the liquid;
  (v) restoring flow through the tube; and
  (vi) returning an unused fraction of the sample of the liquid-solid mixture to the loop slurry reactor; and
(III) when the property of the liquid in the loop slurry reactor has reached a predetermined level, adjusting a polymerization reaction condition.

Embodiment 4. The method or process defined in any one of the preceding embodiments, wherein step (i) thru step (vi) are conducted at a pressure equivalent to vessel (or reactor) pressure.

Embodiment 5. The method or process defined in any one of the preceding embodiments, wherein the time period is any suitable time period, e.g., from about 1 sec to about 1 minute, from about 10 sec to about 45 sec, or from about 15 sec to about 2 minutes.

Embodiment 6. The method or process defined in any one of the preceding embodiments, wherein step (ii) is performed continuously for at least 1 minute, at least 2 minutes, at least 5 minutes, or from 3 to 10 minutes, before step (iii) is conducted.

Embodiment 7. The method or process defined in any one of the preceding embodiments, wherein the analytical instrument is a gas chromatograph, a liquid chromatograph, a spectrometer (or spectrophotometer), or a combination thereof.

Embodiment 8. The method or process defined in any one of the preceding embodiments, wherein the step of transferring the small fraction further comprises a step of vaporizing the liquid.

Embodiment 9. The method or process defined in any one of the preceding embodiments, wherein the step of transferring the small fraction comprises using a carrier gas to transfer the small fraction to the analytical instrument.

Embodiment 10. The method or process defined in any one of the preceding embodiments, further comprising a step of filtering the small fraction prior to the analytical instrument.

Embodiment 11. The method or process defined in any one of the preceding embodiments, wherein the method or process does not include a centrifuging step, a flashing step, or a sieving step.

Embodiment 12. The process defined in any one of embodiments 3-11, wherein in step (i), the sample is withdrawn from a discharge side of a reactor circulation pump.

Embodiment 13. The process defined in any one of embodiments 3-12, wherein in step (vi), the unused fraction is returned to a suction side of a reactor circulation pump.

Embodiment 14. The process defined in any one of embodiments 3-13, wherein a flush of diluent is employed to prevent plugging during step (iii).

Embodiment 15. A polymerization reactor system comprising:
(A) a loop slurry reactor configured to contact a transition metal-based catalyst system with an olefin monomer and an optional olefin comonomer under polymerization reaction conditions to produce an olefin polymer; and
(B) a liquid-solid sampling system comprising:
  (a) an inlet valve and an inlet pipe for withdrawing a liquid-solid mixture from the loop slurry reactor;
  (b) a vertical settling tube downstream of (and connected to) the inlet pipe, the tube configured to segregate the solid to a bottom portion of the tube and for the liquid to occupy an upper portion of the tube (in the absence of flow);
  (c) an outlet valve and an outlet pipe for returning an unused fraction of the liquid-solid mixture to the loop slurry reactor, the outlet pipe downstream of (and connected to) the tube;
  (d) a sample valve and a sample pipe, the sample valve positioned at the upper portion of the tube and configured to withdraw a small fraction of the liquid in the upper portion of the tube;
  (e) an analytical instrument downstream of (and connected to) the sample pipe, the analytical instrument configured to measure a property (at least one) of the liquid; and
  (f) a controller (f1) configured to open the inlet valve and the outlet valve to permit (continuous) flow of the liquid-solid mixture from the loop slurry reactor, through the inlet pipe and the tube, and returning to the loop slurry reactor through the outlet pipe; and (f2) configured to periodically stop flow of the liquid-solid mixture by closing the inlet valve and the outlet valve for a time period sufficient for the solid to settle to the bottom portion of the tube and for the liquid to occupy the upper portion of the tube, and subsequently opening the sample valve to withdraw the small fraction of the liquid.

Embodiment 16. The process or system defined in any one of embodiments 3-15, wherein the polymerization reaction conditions comprise a polymerization reaction temperature in a range from about 60° C. to about 115° C., and a reaction pressure in a range from about 1.38 MPa (200 psig) to about 6.89 MPa (1000 psig), or from about 2.41 MPa (350 psig) to about 5.52 MPa (800 psig).

Embodiment 17. The process or system defined in any one of embodiments 3-16, wherein the transition metal-based catalyst system comprises a solid oxide.

Embodiment 18. The process or system defined in any one of embodiments 3-16, wherein the transition metal-based catalyst system comprises an activator-support, e.g., fluorided silica-coated alumina or sulfated alumina.

Embodiment 19. The process or system defined in any one of embodiments 3-16, wherein the transition metal-based catalyst system comprises chromium impregnated onto a solid oxide or cogelled with a solid oxide.

Embodiment 20. The process or system defined in any one of embodiments 3-19, wherein the transition metal-based catalyst system comprises chromium, vanadium, titanium, zirconium, hafnium, or a combination thereof.

Embodiment 21. The process or system defined in any one of embodiments 3-19, wherein the transition metal-based catalyst system is a chromium-based catalyst system, a Ziegler-Natta based catalyst system, a metallocene-based catalyst system, or a combination thereof.

Embodiment 22. The process or system defined in any one of embodiments 3-21, wherein the olefin monomer comprises a $C_2$-$C_{24}$ olefin.

Embodiment 23. The process or system defined in any one of embodiments 3-21, wherein the olefin monomer comprises propylene.

Embodiment 24. The process or system defined in any one of embodiments 3-21, wherein the olefin monomer comprises ethylene.

Embodiment 25. The process or system defined in any one of embodiments 3-21, wherein the transition metal-based catalyst system is contacted with ethylene and a comonomer comprising 1-butene, 1-hexene, 1-octene, or a mixture thereof.

Embodiment 26. The process or system defined in any one of embodiments 3-25, wherein the olefin polymer is an ethylene homopolymer, an ethylene copolymer, a propylene homopolymer, or a propylene-based copolymer.

Embodiment 27. The process or system defined in any one of embodiments 3-26, wherein the reactor system comprises a single loop slurry reactor.

Embodiment 28. The process or system defined in any one of embodiments 3-26, wherein the reactor system comprises two or more reactors, at least one of which is a loop slurry reactor.

Embodiment 29. The system defined in any one of embodiments 15-28, wherein the inlet valve is connected to a discharge side of a reactor circulation pump.

Embodiment 30. The system defined in any one of embodiments 15-29, wherein the outlet valve is connected to a suction side of a reactor circulation pump.

Embodiment 31. The system defined in any one of embodiments 15-30, further comprising a diluent flush system configured to prevent plugging in the liquid-solid sampling system when the flow of the liquid-solid mixture is stopped.

Embodiment 32. A liquid-solid sampling system comprising:

(a) an inlet valve and an inlet pipe for withdrawing a liquid-solid mixture from a vessel;

(b) a vertical settling tube downstream of (and connected to) the inlet pipe, the tube configured to segregate the solid to a bottom portion of the tube and for the liquid to occupy an upper portion of the tube (in the absence of flow);

(c) an outlet valve and an outlet pipe for returning an unused fraction of the liquid-solid mixture to the vessel, the outlet pipe downstream of (and connected to) the tube;

(d) a sample valve and a sample pipe, the sample valve positioned at the upper portion of the tube and configured to withdraw a small fraction of the liquid in the upper portion of the tube;

(e) an analytical instrument downstream of (and connected to) the sample pipe, the analytical instrument configured to measure a property (at least one) of the liquid; and (f) a controller (f1) configured to open the inlet valve and the outlet valve to permit (continuous) flow of the liquid-solid mixture from the vessel, through the inlet pipe and the tube, and returning to the vessel through the outlet pipe; and (f2) configured to periodically stop flow of the liquid-solid mixture by closing the inlet valve and the outlet valve for a time period sufficient for the solid to settle to the bottom portion of the tube and for the liquid to occupy the upper portion of the tube, and subsequently opening the sample valve to withdraw the small fraction of the liquid.

Embodiment 33. The system defined in embodiment 32, wherein the vessel is a loop slurry reactor.

Embodiment 34. The system defined in any one of embodiments 15-33, further comprising a carrier gas inlet that enters the sample pipe after the sample valve and before the analytical instrument.

Embodiment 35. The system defined in any one of embodiments 15-34, further comprising a filter assembly before the analytical instrument.

Embodiment 36. The system defined in any one of embodiments 15-35, wherein the system does not contain a centrifuge, a flash drum, or a sieve.

Embodiment 37. The system defined in any one of embodiments 15-36, wherein the settling tube is configured to operate at a pressure equivalent to vessel (or reactor) pressure.

Embodiment 38. The system defined in any one of embodiments 15-37, wherein the controller is further configured to perform (f1) continuously for at least 1 minute, at least 2 minutes, at least 5 minutes, or from 3 to 10 minutes, before (f2) is conducted.

Embodiment 39. The system defined in any one of embodiments 15-38, wherein the controller comprises a processing unit.

Embodiment 40. The system defined in any one of embodiments 15-39, wherein the analytical instrument is a gas chromatograph, a liquid chromatograph, a spectrometer (or spectrophotometer), or a combination thereof.

Embodiment 41. The method, process, or system defined in any one of the preceding embodiments, wherein the density difference between the solid and the liquid is any suitable density difference, e.g., at least 0.1 g/cc, at least 0.2 g/cc, at least 0.5 g/cc, in a range from about 0.1 g/cc to about 3 g/cc, or from about 0.2 g/cc to about 1 g/cc.

Embodiment 42. The method, process, or system defined in any one of the preceding embodiments, wherein the liquid-solid mixture is a slurry of solids in a liquid diluent.

Embodiment 43. The method, process, or system defined in any one of the preceding embodiments, wherein the small fraction of the liquid is substantially free of solids, e.g., less than 5 wt. % solids, less than 1 wt. % solids, or less than 0.1 wt. % solids.

Embodiment 44. The method, process, or system defined in any one of the preceding embodiments, wherein the amount of the small fraction of the liquid removed is less than 5 wt. %, less than 2 wt. %, less than 1 wt. %, or less than 0.5 wt. %, based on the total amount of the liquid-solid mixture in the settling tube.

We claim:

1. A process for operating a polymerization reactor system, the process comprising:
   (I) contacting a transition metal-based catalyst system with an olefin monomer and an optional olefin comonomer in a loop slurry reactor within the polymerization reactor system under polymerization reaction conditions to produce an olefin polymer, the loop slurry reactor containing a liquid-solid mixture;
   (II) measuring a property of the liquid in the loop slurry reactor via a method comprising the steps of:
      (i) withdrawing a sample of the liquid-solid mixture from the loop slurry reactor;
      (ii) flowing the sample of the liquid-solid mixture through a vertical settling tube;
      (iii) periodically stopping the flow of the sample of the liquid-solid mixture in the tube for a time period sufficient for the solid to settle to a bottom portion of the tube and for the liquid to occupy an upper portion of the tube;
      (iv) removing a small fraction of the liquid in the upper portion of the tube and transferring the small fraction of the liquid to an analytical instrument for measuring the property of the liquid;
      (v) restoring flow through the tube; and
      (vi) returning an unused fraction of the sample of the liquid-solid mixture to the loop slurry reactor; and
   (III) when the property of the liquid in the loop slurry reactor has reached a predetermined level, adjusting a polymerization reaction condition.

2. The process of claim 1, wherein the liquid-solid mixture is a slurry of solids in a liquid diluent.

3. The process of claim 1, wherein:
   the time period is from about 1 sec to about 1 min; and
   a density difference between the solid and the liquid is at least 0.2 g/cc.

4. The process of claim 1, wherein:
   the small fraction of the liquid contains less than 5 wt. % solids; and
   the amount of the small fraction of the liquid removed is less than 5 wt. %, based on the total amount of the liquid-solid mixture in the settling tube.

5. The process of claim 1, wherein:
   the transition metal-based catalyst system is a chromium-based catalyst system, a Ziegler-Natta based catalyst system, a metallocene-based catalyst system, or a combination thereof; and
   the olefin monomer comprises a $C_2$-$C_{24}$ olefin.

6. The process of claim 1, wherein the transition metal-based catalyst system is contacted with ethylene and an olefin comonomer comprising 1-butene, 1-hexene, 1-octene, or a mixture thereof.

7. The process of claim 1, wherein the polymerization reaction conditions comprise a polymerization reaction temperature in a range from about 60° C. to about 115° C., and a reaction pressure in a range from about 1.38 MPa to about 6.89 MPa.

8. The process of claim 1, wherein:
   step (ii) is performed continuously for at least 1 min before step (iii) is conducted; and
   step (iii) is conducted at a pressure equivalent to that of the loop slurry reactor.

9. The process of claim 1, wherein:
   in step (i), the sample is withdrawn from a discharge side of a reactor circulation pump; and
   in step (vi), the unused fraction is returned to a suction side of a reactor circulation pump.

10. The process of claim 1, wherein the process does not include a centrifuging step, a flashing step, or a sieving step.

11. A polymerization reactor system comprising:
    (A) a loop slurry reactor configured to contact a transition metal-based catalyst system with an olefin monomer and an optional olefin comonomer under polymerization reaction conditions to produce an olefin polymer; and
    (B) a liquid-solid sampling system comprising:
       (a) an inlet valve and an inlet pipe for withdrawing a liquid-solid mixture from the loop slurry reactor;
       (b) a vertical settling tube downstream of the inlet pipe, the tube configured to segregate the solid to a bottom portion of the tube and for the liquid to occupy an upper portion of the tube;
       (c) an outlet valve and an outlet pipe for returning an unused fraction of the liquid-solid mixture to the loop slurry reactor, the outlet pipe downstream of the tube;
       (d) a sample valve and a sample pipe, the sample valve positioned at the upper portion of the tube and configured to withdraw a small fraction of the liquid in the upper portion of the tube;
       (e) an analytical instrument downstream of the sample pipe, the analytical instrument configured to measure a property of the liquid; and
       (f) a controller (f1) configured to open the inlet valve and the outlet valve to permit flow of the liquid-solid mixture from the loop slurry reactor, through the inlet pipe and the tube, and returning to the loop slurry reactor through the outlet pipe; and (f2) configured to periodically stop flow of the liquid-solid mixture by closing the inlet valve and the outlet valve for a time period sufficient for the solid to settle to the bottom portion of the tube and for the liquid to occupy the upper portion of the tube, and subsequently opening the sample valve to withdraw the small fraction of the liquid.

12. The system of claim 11, wherein the reactor system comprises a single loop slurry reactor.

13. The system of claim 11, wherein the reactor system comprises two or more reactors, at least one of which is the loop slurry reactor.

14. The system of claim 11, wherein the analytical instrument is a gas chromatograph, a liquid chromatograph, a spectrometer, or a combination thereof.

15. The system of claim 14, further comprising a filter assembly before the analytical instrument.

16. The system of claim 11, further comprising a carrier gas inlet that enters the sample pipe after the sample valve and before the analytical instrument.

17. The system of claim 11, wherein the settling tube is configured to operate at a pressure equivalent to that of the loop slurry reactor.

18. The system of claim 11, wherein:
    the time period is from about 15 sec to about 2 min;
    a density difference between the solid and the liquid is in a range from about 0.2 g/cc to about 1 g/cc;

the small fraction of the liquid is less than 5 mL;

the small fraction contains less than 1 wt. % solids; and the amount of the small fraction is less than 2 wt. %, based on the total amount of the liquid-solid mixture in the settling tube.

19. The system of claim 11, wherein the system does not contain a centrifuge, a flash drum, or a sieve.

20. A method for measuring a property of a liquid in a vessel containing a liquid-solid mixture, the method comprising:

(i) withdrawing a sample of the liquid-solid mixture from the vessel;

(ii) flowing the sample of the liquid-solid mixture through a vertical settling tube;

(iii) periodically stopping the flow of the sample of the liquid-solid mixture in the tube for a time period sufficient for the solid to settle to a bottom portion of the tube and for the liquid to occupy an upper portion of the tube;

(iv) removing a small fraction of the liquid in the upper portion of the tube and transferring the small fraction of the liquid to an analytical instrument for measuring the property of the liquid;

(v) restoring flow through the tube; and (vi) returning an unused fraction of the sample of the liquid-solid mixture to the vessel.

\* \* \* \* \*